US012582550B2

(12) United States Patent
Gliner et al.

(10) Patent No.: US 12,582,550 B2
(45) Date of Patent: Mar. 24, 2026

(54) DETERMINING FLUID FLOW RATE IN A PHACOEMULSIFICATION PROBE

(71) Applicant: JOHNSON & JOHNSON SURGICAL VISION, INC., Irvine, CA (US)

(72) Inventors: Vadim Gliner, Haifa (IL); Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 41 days.

(21) Appl. No.: 18/420,607

(22) Filed: Jan. 23, 2024

(65) Prior Publication Data

US 2025/0235353 A1      Jul. 24, 2025

(51) Int. Cl.
  *A61F 9/007*     (2006.01)
  *G01F 1/36*      (2006.01)
  *G16H 40/63*     (2018.01)
  *A61B 90/00*     (2016.01)

(52) U.S. Cl.
  CPC ...... *A61F 9/00745* (2013.01); *A61F 9/00763* (2013.01); *G01F 1/36* (2013.01); *G16H 40/63* (2018.01); *A61B 2090/064* (2016.02); *A61B 2217/005* (2013.01); *A61B 2217/007* (2013.01)

(58) Field of Classification Search
  CPC .... A61F 9/00745; A61F 9/00763; G01F 1/36; G16H 40/63; A61B 2090/064; A61B 2217/005; A61B 2217/007
  See application file for complete search history.

(56) References Cited

U.S. PATENT DOCUMENTS

| | | | |
|---|---|---|---|
| 8,264,363 B2 | 9/2012 | DelCastillo et al. | |
| 8,718,957 B2 | 5/2014 | Furmanski et al. | |
| 11,185,623 B2 | 11/2021 | Ovchinnikov et al. | |
| 11,338,076 B2 | 5/2022 | Kusters et al. | |
| 2011/0112595 A1 | 5/2011 | Solem | |
| 2020/0405955 A1 | 12/2020 | Shah et al. | |
| 2024/0207092 A1* | 6/2024 | Govari | A61F 9/00736 |
| 2024/0342003 A1* | 10/2024 | Govari | A61F 9/00745 |

FOREIGN PATENT DOCUMENTS

| | | |
|---|---|---|
| DE | 3220539 A1 | 12/1983 |
| EP | 0164506 A1 | 12/1985 |

* cited by examiner

*Primary Examiner* — Brooke Labranche

(57) ABSTRACT

Apparatus for determining a fluid flow rate in a channel of a phacoemulsification probe, including a first pressure sensor, coupled with fluid in the channel at a first position. A second pressure sensor couples with the fluid in the channel at a second position, at a preset distance from the first position, and the fluid flows from the first to the second position. A processor acquires from the first pressure sensor first indications of a pressure profile of a portion of the fluid passing the first pressure sensor, and acquires from the second pressure sensor second indications of a pressure profile of the fluid passing the second pressure sensor. The processor correlates the first and second indications to determine a time for the fluid portion to travel from the first to the second position, and calculates the fluid flow rate in response to the time and the preset distance.

30 Claims, 5 Drawing Sheets

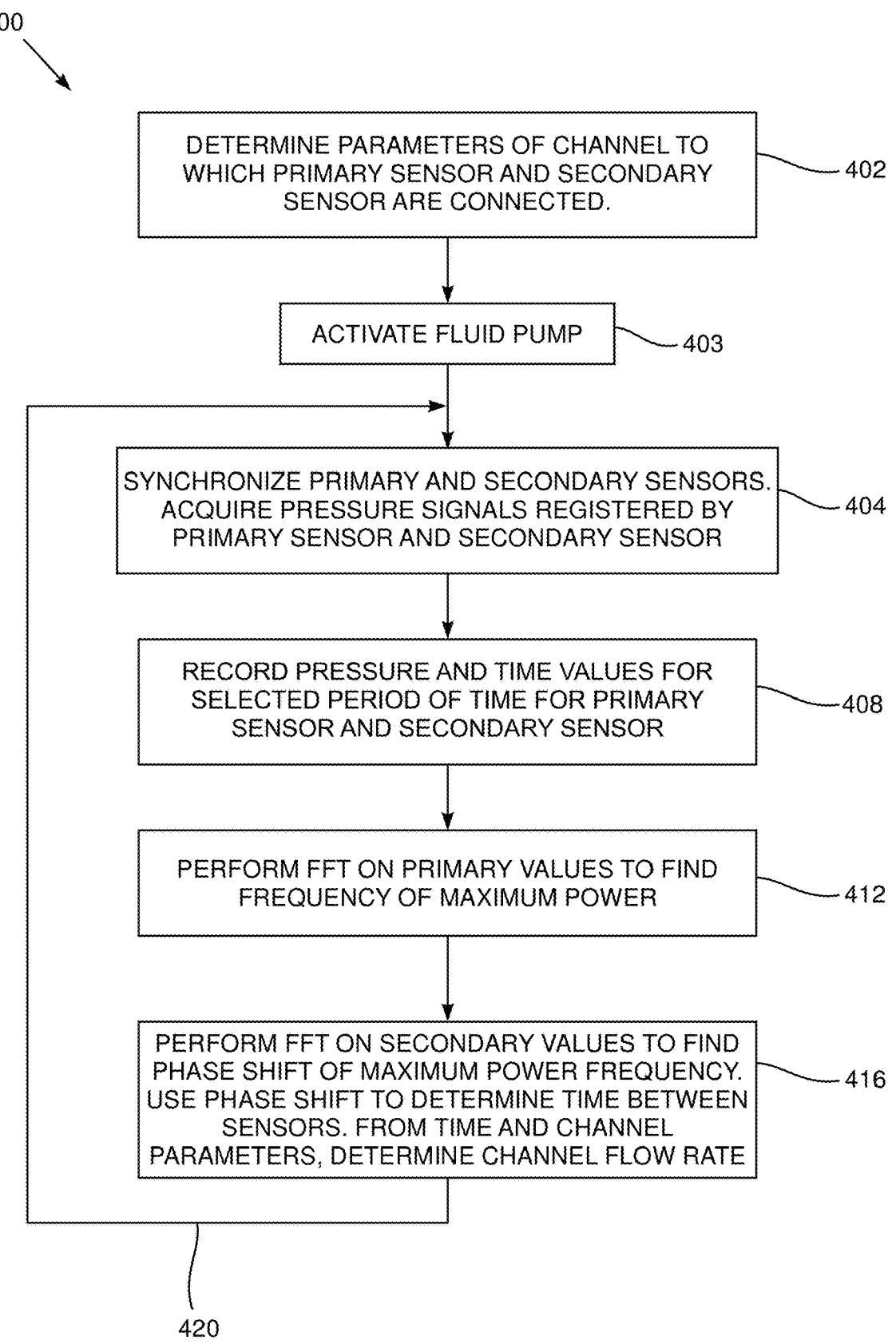

400

DETERMINE PARAMETERS OF CHANNEL TO WHICH PRIMARY SENSOR AND SECONDARY SENSOR ARE CONNECTED. —402

ACTIVATE FLUID PUMP —403

SYNCHRONIZE PRIMARY AND SECONDARY SENSORS. ACQUIRE PRESSURE SIGNALS REGISTERED BY PRIMARY SENSOR AND SECONDARY SENSOR —404

RECORD PRESSURE AND TIME VALUES FOR SELECTED PERIOD OF TIME FOR PRIMARY SENSOR AND SECONDARY SENSOR —408

PERFORM FFT ON PRIMARY VALUES TO FIND FREQUENCY OF MAXIMUM POWER —412

PERFORM FFT ON SECONDARY VALUES TO FIND PHASE SHIFT OF MAXIMUM POWER FREQUENCY. USE PHASE SHIFT TO DETERMINE TIME BETWEEN SENSORS. FROM TIME AND CHANNEL PARAMETERS, DETERMINE CHANNEL FLOW RATE —416

DETERMINING FLUID FLOW RATE IN A PHACOEMULSIFICATION PROBE

FIELD OF THE DISCLOSURE

This disclosure relates generally to phacoemulsification, and specifically to operation of a phacoemulsification probe.

BACKGROUND

Phacoemulsification may be used in cataract surgery, during which the eye's internal lens is emulsified with an ultrasonic handpiece and aspirated from the eye. During the surgery the eye may also be irrigated. Typically, an aspiration pump provides the aspiration, and a separate irrigation pump provides the irrigation, and the flows from both pumps may affect the eye's internal pressure.

BRIEF DESCRIPTION OF THE DRAWINGS

The present disclosure will be understood from the following detailed description, taken in conjunction with the drawings in which:

FIG. 5 is a flowchart of an algorithm of steps performed to find the flow rate of irrigation fluid, according to an alternative example of the present disclosure.

DESCRIPTION OF EXAMPLES

Overview

Figure 1:
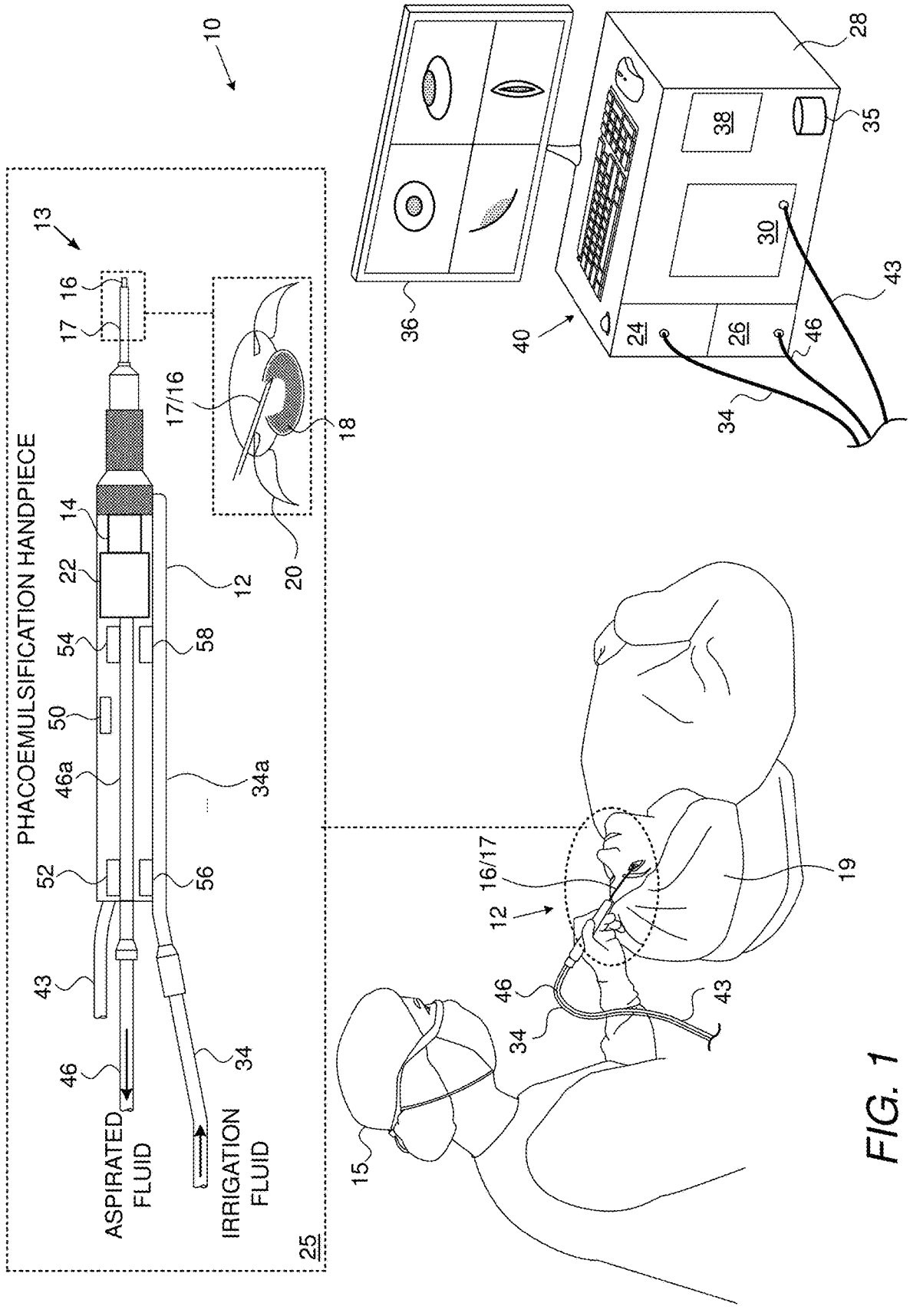
FIG. 1 is a pictorial view of a phacoemulsification apparatus, according to an example of the present disclosure.

A phacoemulsification procedure on the eye of a patient to remove the natural lens of the eye, may be carried out using a phacoemulsification handpiece, which comprises a hollow needle having a distal tip that is vibrated ultrasonically. The tip is placed within the capsular bag, and the vibrations are used to break the lens into smaller sections which are emulsified.

The handpiece comprises an aspiration channel, a proximal end of the channel being coupled with an aspiration pump via aspiration tubing, the distal end of the channel being coupled with the hollow needle. During the procedure the pump aspirates the emulsified material via the hollow needle and aspiration channel.

In addition to the aspiration provided by the pump, during the procedure the eye is separately irrigated using an irrigation pump. The handpiece has an irrigation channel, a proximal end of which is coupled with the irrigation pump via irrigation tubing, the distal end of the channel being coupled with a sleeve surrounding at least a portion of the distal tip of the hollow needle. During the procedure the irrigation pump transfers irrigation fluid, typically a balanced salt solution, via the irrigation tubing, irrigation channel and the sleeve to the eye.

The aspiration flow rate and the irrigation flow rate both affect the intra-ocular pressure (IOP) of the eye, so that to keep the IOP within required limits to prevent damaging structures of the eye it is necessary to measure both the aspiration flow and the irrigation flow at the eye.

A processor operates both the aspiration pump and the irrigation pump, and so is able to set a nominal rate of flow for each of the pumps. However, this is not the same as the actual flow rate at, or even close to, the eye, because typically both pump rates oscillate, the tubing lines are relatively long, and the channels are narrow, having diameters of the order of a millimeter. The flow rate may be measured by monitoring the pressure in the channel, and in some cases, the difference between the actual and nominal flow rate may lead to a pressure difference of 100 mmHg.

Examples of the present disclosure provide accurate measures of the flow rate by providing two pressure sensors in each of the channels of the handpiece.

Considering the irrigation channel, a first pressure sensor is placed at a proximal location of the channel, and a second pressure sensor is placed at a distal location, at a known distance from the first sensor. The processor records the pressure variations registered by each of the sensors, and by comparing the records, the processor is able to find the time taken for any particular pressure variation to travel from the first sensor to the second sensor. Using the time and the known distance, the processor calculates the speed of the irrigation fluid. By using known dimensions of the irrigation channel, or alternatively by pre-calibrating the channel with known fluid flow rates, the processor may calculate the rate of flow of the irrigation fluid from the calculated irrigation fluid speed.

For the aspiration channel, a first pressure sensor is placed at a proximal location of the channel and a second sensor is placed at a distal location at a known distance from the first sensor. The processor compares the pressure variations of each of the sensors, to find the time taken for a particular pressure variation to travel from the first to the second sensor. From the time taken the processor calculates the speed, and, using known dimensions of the aspiration channel or by pre-calibration of the channel, the flow rate of the aspiration fluid.

SYSTEM DESCRIPTION

In the following description, like elements are identified by the same numeral, and are differentiated, where required, by having a letter attached as a suffix to the numeral.

Figure 2:
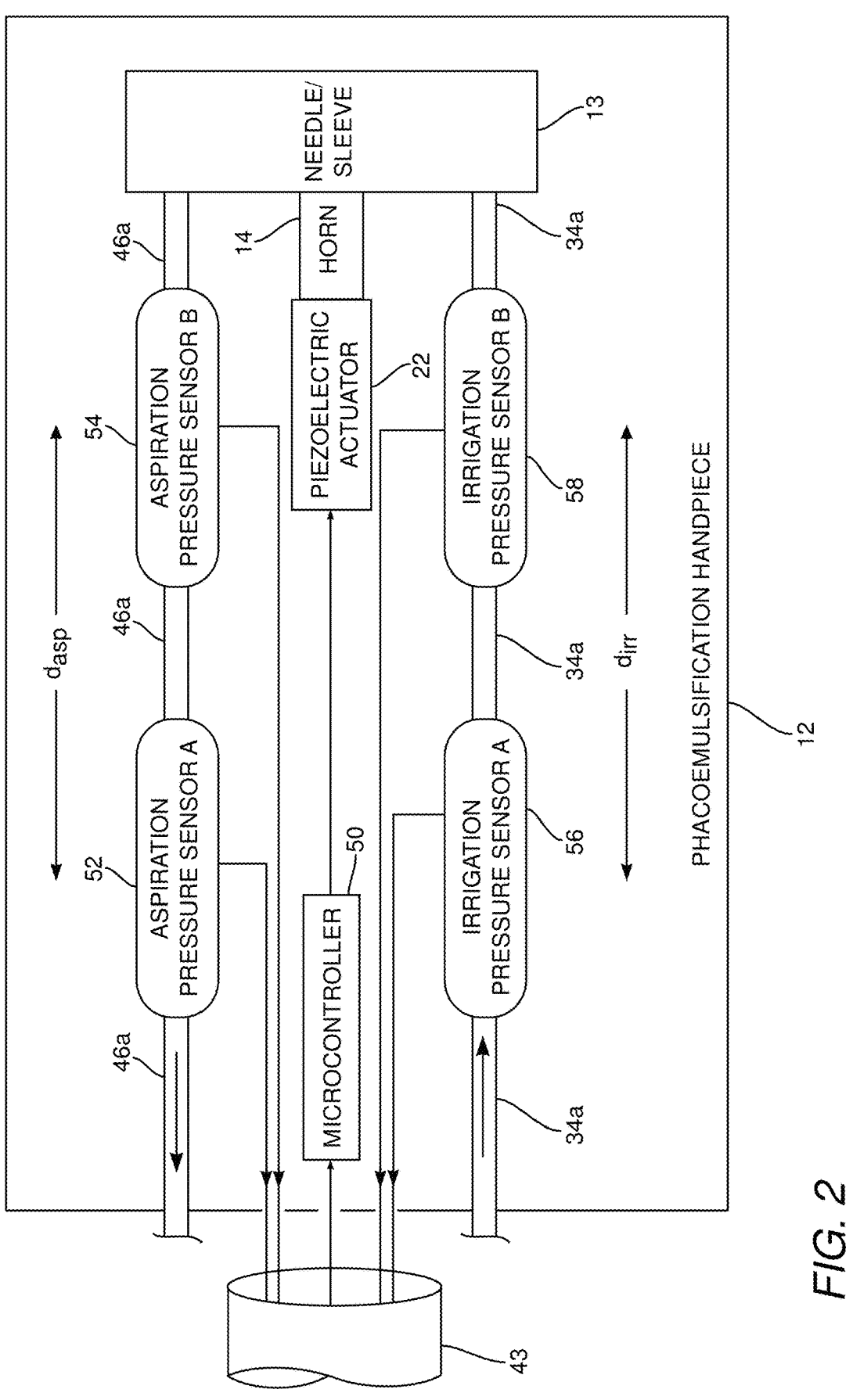
FIG. 2 is a block diagram of elements of a phacoemulsification probe/handpiece, according to an example of the present disclosure.

FIG. 1 is a pictorial view of a phacoemulsification apparatus 10, and FIG. 2 is a block diagram of elements of a phacoemulsification probe/handpiece 12 that is a part of the apparatus, according to an example of the present disclosure.

FIG. 1 includes an inset 25, and as shown in the figure and the inset apparatus 10 includes phacoemulsification probe/handpiece 12 that comprises a hollow needle 16 and a coaxial irrigation sleeve 17. Irrigation sleeve 17 at least partially surrounds the needle 16 and creates a fluid pathway between the external wall of the needle 16 and the internal wall of the sleeve 17. Needle 16 and sleeve 17 are also herein termed a needle-sleeve combination 13.

Needle 16 is configured to be inserted into a lens 18 of an eye 20 of a patient 19. Needle 16 is mounted on a horn 14 of probe 12, and is shown in inset 25 as a straight needle. However, any suitable needle may be used with the phacoemulsification probe 12, for example, a curved or bent tip needle that is commercially available from Johnson & Johnson Surgical Vision, Inc., Irvine, CA, USA.

A physician 15 holds handpiece 12 so as to perform a phacoemulsification procedure on the eye 20 of patient 19.

The physician may activate the handpiece using a foot pedal (not shown in the figures). Handpiece 12 comprises a piezoelectric actuator 22, which is configured to vibrate horn 14 and needle 16 in one or more vibration modes of the combined horn and needle. During the phacoemulsification procedure the vibration of needle 16 is used to break up natural lens 18 into small pieces.

Elements of apparatus 10 are under overall control of a processor 38 in a console 28. Functions of processor 38 are described in more detail below, and at least some of the functions of processor 38 may be carried out by suitable software stored in a memory 35. The software may be downloaded to a device in electronic form, over a network, for example. Alternatively, or additionally, the software may be stored in tangible, non-transitory computer-readable storage media, such as optical, magnetic, or electronic memory. Some or all of the functions of processor 38 may be combined in a single physical component or, alternatively, implemented using multiple physical components. The physical components may comprise hard-wired or programmable devices, or a combination of the two.

Actuator 22 is powered by a driving module 30 in console 28. Module 30, under overall control of processor 38, is configured to provide the power to the actuator 22, via a microcontroller 50 located in the handpiece 12. Power for microcontroller 50, as well as control signals for the microcontroller, is delivered to the microcontroller by a cable 43 from driving module 30.

During the phacoemulsification procedure, an irrigation pump 24, which may be in or outside console 28, pumps irrigation fluid through an irrigation channel 34a in handpiece 12 to irrigation sleeve 17 so as to irrigate the eye. The fluid is pumped via an irrigation tubing line 34, running from the pump, that is connected to channel 34a of the probe 12.

An aspiration pump 26, which also may be located in or outside console 28, aspirates aspiration fluid, comprising eye fluid and waste matter (e.g., emulsified parts of the lens), from the patient's eye 20 via needle 16, through an aspiration channel 46a in handpiece 12. Aspiration pump 26 produces a vacuum that is connected from the pump to aspiration channel 46a by an aspiration tubing line 46.

Pumps 24 and 26 may be any pump known in the art (e.g., a peristaltic pump or a progressive cavity pump), and the pumps are both under overall control of processor 38.

A first aspiration pressure sensor 52, also herein termed aspiration pressure sensor A, is coupled with aspiration channel 46a, in a proximal section of the channel, so as to couple with the aspiration fluid in the channel. A second aspiration pressure sensor 54, also herein termed aspiration pressure sensor B, is also coupled with aspiration channel 46a, in a distal section of the channel, so as to couple with the aspiration fluid in the channel. The two aspiration pressure sensors are located at a known distance $d_{asp}$ between each other, measured along aspiration channel 46a.

A first irrigation pressure sensor 56, also herein termed irrigation pressure sensor A, is coupled with irrigation channel 34a, in a proximal section of the channel, so as to couple with the irrigation fluid in the channel. A second irrigation pressure sensor 58, also herein termed irrigation pressure sensor B, is also coupled with irrigation channel 34a, in a distal section of the channel, so as to couple with the irrigation fluid in the channel. The two irrigation pressure sensors are located at a known distance $d_{irr}$ from each other, measured along irrigation channel 34a.

In a disclosed example $d_{asp}$ and $d_{irr}$ are both approximately 20 mm. In an alternative example $d_{asp}$ and $d_{irr}$ may each be in a range from approximately 10 mm to approximately 30 mm.

The signals generated by the two aspiration sensors, sensor 52 and sensor 54, and by the two irrigation sensors, sensor 56 and sensor 58, are provided via cable 43, as illustrated in FIG. 1 and FIG. 2, to processor 38. As is described below, processor 38 uses the signals from the aspiration sensors to calculate the aspiration flow rate, and the signals from the irrigation sensors to calculate the irrigation flow rate.

The apparatus illustrated in FIG. 1 may include further elements, which are omitted for clarity of presentation. For example, physician 15 typically performs the procedure using a stereo-microscope or magnifying glasses, neither of which are shown. Physician 15 may use other surgical tools, in addition to probe 12, which are also not shown to maintain clarity and simplicity.

Processor 38 may present setting and parameter information of the phacoemulsification procedure on a display 36. In an example, user interface 40 and display 36 may be one and the same, such as a touch screen graphical user interface.

Processor 38 may receive user-based commands via a system user interface 40, which may include, but is not limited to, setting and/or adjusting a vibration mode and/or a frequency of piezoelectric actuator 22, setting and/or adjusting a stroke amplitude of needle 16, and setting and/or adjusting an irrigation flow rate and an aspiration flow rate of irrigation pump 24 and aspiration pump 26.

While physician 15 may set the irrigation flow rate and the aspiration flow rate to selected values, or may set the rates to respective default values, it will be understood that the actual rates of flow of both the irrigation fluid and the aspiration fluid may vary with time. The pumps themselves do not deliver the fluid at a constant rate, but rather vary the rate about a nominal set value in an oscillatory manner. In addition, flexing of the tubing connected to the pumps, as well as changes in the tubing terminations at the eye due to the procedure being performed, may cause the flow rate to change.

Because during a phacoemulsification procedure there is a non-zero flow rate of both the aspiration and the irrigation fluid, the pressure registered by the aspiration and irrigation sensors is not equal to the IOP. (In the theoretical case of a zero flow rate, since there is fluid communication between the intra-ocular eye fluid, the aspiration fluid, and the irrigation fluid, the pressure measured by the sensors would equal the IOP.)

The changes in flow rate lead to corresponding changes in pressure in the fluid being transferred, and, as is described below, examples of the present disclosure use the changes of pressure in order to calculate accurate values of the flow rate.

Figure 3:
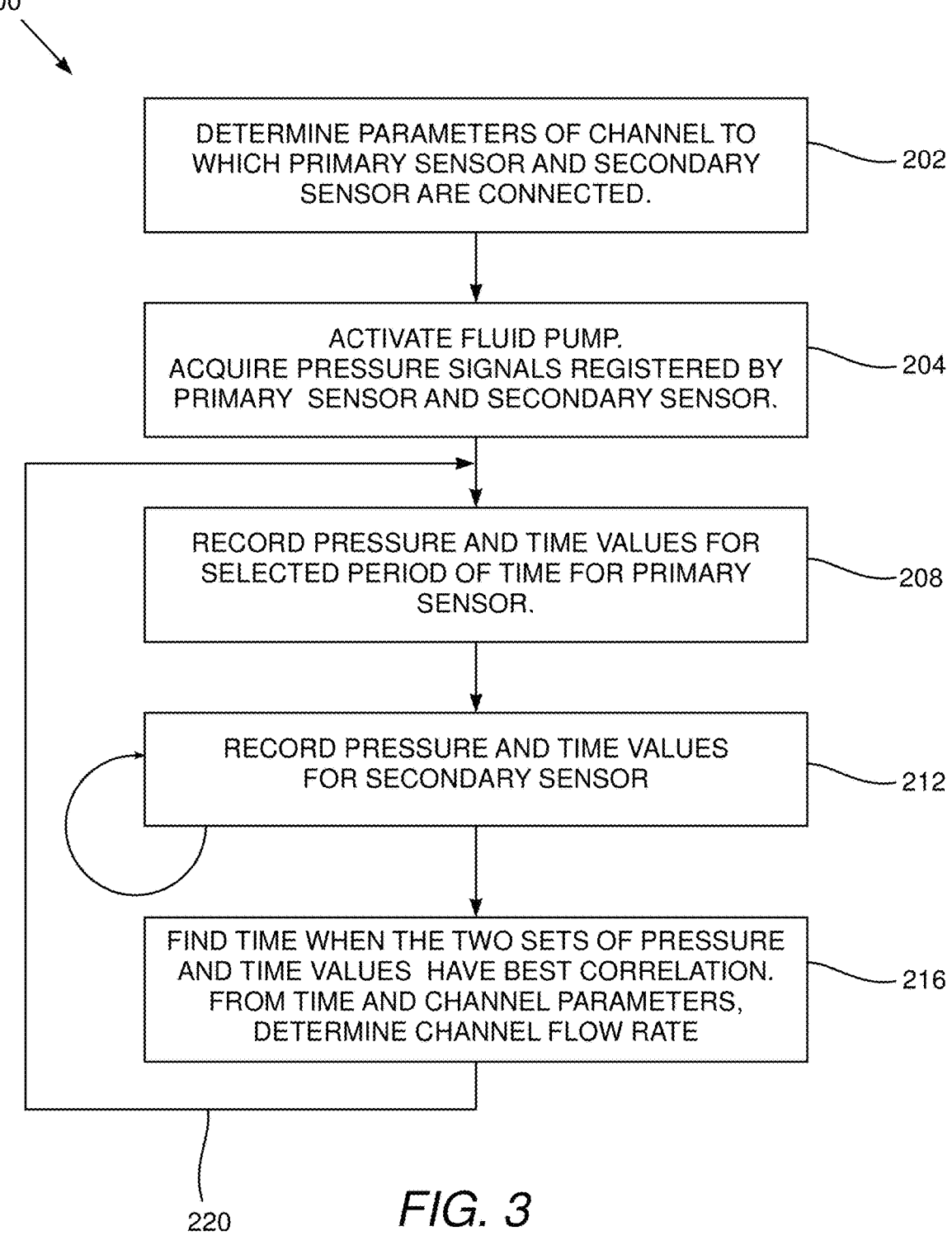
FIG. 3 is a flowchart of an algorithm of steps performed to find the flow rate of irrigation fluid, according to an example of the present disclosure.
Figures 4A, 4B:
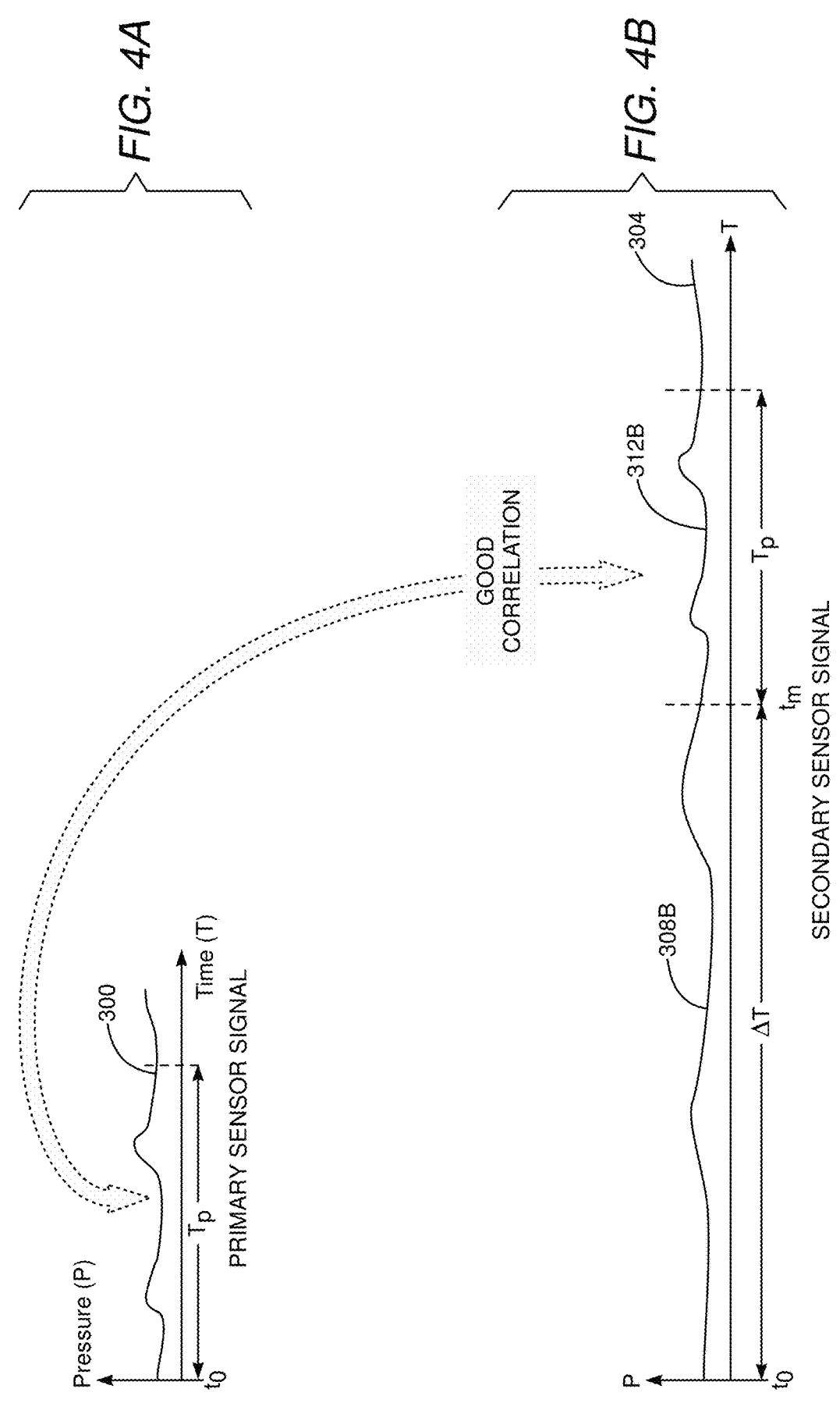
FIGS. 4A and 4B are schematic graphs illustrating the steps of the flowchart of FIG. 3, according to an example of the present disclosure.

FIG. 3 is a flowchart 200 of an algorithm of steps performed to find the flow rate of irrigation fluid in irrigation channel 34a of probe 12, and FIGS. 4A and 4B are schematic graphs illustrating the steps, according to an example of the present disclosure.

For clarity, flowchart 200 has been written to describe finding the flow rate of the irrigation fluid, and those having ordinary skill in the art will be able to adapt the description, mutatis mutandis, to find the flow rate of the aspiration fluid.

In an initial step 202, processor 38 determines dimensional parameters of the irrigation channel which, when known, enable the processor to calculate the irrigation flow rate from the time of travel of the irrigation fluid between the primary sensor and the secondary sensor of the channel. The dimensional parameters comprise the effective distance, a preset distance, between the two sensors, measured along the channel, as well as the effective cross-sectional area of the channel, and may be calculated using known sensor locations and dimensions of the channel or, alternatively, by pre-calibration of the channel using known fluid flow rates.

In an activation step 204 irrigation pump 24 is activated, to begin irrigating irrigation fluid to eye 20. Once activated, processor 38 begins acquiring signals from irrigation pressure sensor A, and from irrigation pressure sensor B. The irrigation fluid flows past both sensors, first past irrigation sensor A, then past irrigation sensor B, and in the following description the first irrigation sensor, irrigation sensor A, is also termed the primary sensor, and the second irrigation sensor, irrigation sensor B, is also termed the secondary sensor. (For the aspiration fluid flow, which flows in the opposite direction to the irrigation flow, aspiration pressure sensor B is the primary sensor, and aspiration pressure sensor A is the secondary sensor.)

In a primary signal recordation step 208, while continuously acquiring signals from the primary sensor, processor 38 records, for a preselected period of time $T_p$ while irrigation pump 24 is activated, a set of values of pressure and respective times registered by the primary sensor as the irrigation fluid flows past it.

In a disclosed example the preselected period $T_p$ is 1 second, but other examples may have smaller or larger periods of time, e.g., the period of time may be 1-5 seconds with smaller increments as well. The set of pressure time values acts as a "fingerprint," i.e., a pressure profile, of the portion of the fluid flowing past the primary sensor in the preselected period.

A graph 300 of pressure P vs. time T, in FIG. 4A schematically illustrates the set of values recorded in time period $T_p$ by processor 38 in step 208. The recorded set of values is assumed to begin at a time to, and corresponds to the pressure profile of the fluid.

In a secondary signal recordation step 212, as processor 38 is acquiring signals registered by the secondary sensor, it continuously selects, on an iterative basis, the most recent set of signals acquired during a time period equal to the preselected period, and stores an initial time when the set is acquired. The circular arrow in the flowchart, at step 212, illustrates the iterative nature of the step.

In a correlation step 216, processor 38 correlates each set of the secondary signals with the primary set of signals recorded in step 208, to determine a correlation coefficient relating the two sets of signals, and checks for good correlation. Cross-correlation is performed to determine the point in time that the pressure readings on primary pressure sensor best align with the pressure profile recorded on the secondary pressure sensor.

FIG. 4B schematically illustrates pressure P vs. time T values for an extended period of time for the secondary sensor. A graph 308B schematically shows the pressure P vs. time T values acquired from the secondary pressure sensor by processor 38, and a section 312B of the graph, beginning at a time $t_m$ and having a temporal length $T_p$, corresponds to the set of secondary signals checked by the processor. Processor 38 compares the set of pressure time values of the secondary pressure sensor, represented by section 312B, i.e., the pressure profile, with the set of pressure time signals of the primary pressure sensor, illustrated by graph 300, to find the correlation coefficient.

When there is good correlation, e.g., in a disclosed example if the correlation coefficient relating the two pressure-time sets is greater than or equal to 0.85, the processor stores the initial time, $t_m$, of the secondary signal set. FIG. 4B illustrates an occurrence of good correlation: the pressure profile of graph 300 has two "humps" separated temporally, and the pressure profile of graph 312B has two similar humps with a similar temporal distribution.

It will be understood that the difference in time $\Delta t$ given by expression (1):

$$\Delta t \overset{def}{=} (t_m - t_0) \tag{1}$$

corresponds to the time taken for the portion of fluid having pressures recorded in step 204 to travel from the primary sensor to the secondary sensor.

The fluid flow rate is directly proportional to $\Delta t$. Thus, processor 38 is able to calculate the fluid flow rate according to expression (2):

$$F = k \cdot \Delta t \tag{2}$$

where F is the fluid flow rate,
$\Delta t$ is the difference in time given by expression (1), and
k is a constant of proportionality derived from the parameters registered in initial step 202; k includes the preset distance registered in step 202.

Processor 38 may provide an indication of the value of the fluid flow rate derived from expression (2) to physician 15, for example as an alphanumeric and/or a graphical representation, on display 36. In addition, or in another example, the calculated fluid flow rate may be used to control one or more parameters of system 10, thereby controlling the IOP in the eye or at or near the needle-sleeve combination 13.

Alternatively or additionally, in the case of the aspiration fluid, when the primary aspiration pressure sensor, i.e., the aspiration pressure sensor closest to the eye, is assumed to give an indication of the IOP of the eye, processor 38 may use the signal provided by the sensor, and the flow rate provided by expression (2), in a negative feedback loop controlling the aspiration pump rate so as to maintain the IOP within acceptable limits.

As shown by a line 220 in flowchart 200, steps 208-216 are reiterated, so that the fluid flow rate is continuously monitored during the procedure performed by physician 15.

In a disclosed example the reiteration of steps 208-216 is performed by stepping the beginning of the recording time of step 208 by a pre-defined time. In one example the pre-defined time is 3 ms, but in other examples the pre-defined time may be smaller or larger than 3 ms.

FIG. 5 is a flowchart 400 of an algorithm of steps performed to find the flow rate of irrigation fluid in irrigation channel 34a of probe 12, according to an alternative example of the present disclosure.

For clarity, as for flowchart 200, flowchart 400 has been written to describe finding the flow rate of the irrigation fluid, and those having ordinary skill in the art will be able to adapt the description, mutatis mutandis, to find the flow rate of the aspiration fluid.

An initial step 402, wherein processor 38 determines dimensional parameters of the irrigation channel, is substantially as described above for initial step 202.

In a first activation step 403, processor 38 activates irrigation pump 24.

In a second activation step 404, after activating irrigation pump 24, processor 38 synchronizes irrigation pressure sensor A, which acts as the primary sensor, and irrigation pressure sensor B, which acts as the secondary sensor. Processor 38 then begins acquiring signals from the two sensors. (For the aspiration fluid flow, which flows in the opposite direction to the irrigation flow, aspiration pressure sensor B is the primary sensor, and aspiration pressure sensor A is the secondary sensor.)

In a signal recordation step 408, processor 38 records, for a preselected period of time $T_p$ (illustrated in FIGS. 4A and 4B), a set of values of pressure and respective times registered by the primary sensor, and a set of pressure time values registered by the secondary sensor. Processor 38 records the values from the two sensors at the same time, i.e., simultaneously.

In a disclosed example the preselected period $T_p$ is in a range of approximately 1 second to approximately 5 seconds, but other examples may have smaller or larger periods outside this range.

In a first analysis step 412, processor 38 performs a fast Fourier transform (FFT) on the recorded signals of the primary sensor to convert the signals to the frequency domain. From the FFT, processor 38 finds a frequency $f_p$ of the recorded set having a maximum power. In the analysis the processor also finds a measure for the phase of the maximum power frequency.

In a second analysis step 416 processor 38 performs an FFT on the recorded signals of the secondary sensor. Using the FFT, the processor finds a phase shift $\varphi$ of the secondary sensor maximum power frequency $f_p$ with respect to the phase of the $f_p$ of the primary sensor. In a disclosed example processor 38 applies the Goertzel algorithm to evaluate the phase shift $\varphi$.

Processor 38 then converts the phase shift $\varphi$ for the frequency $f_p$ to a value of time T.

It will be understood that the time T corresponds to the time taken for fluid to transfer from the primary sensor to the secondary sensor.

As described above for step 202 of flowchart 200, the fluid flow rate is directly proportional to T. Thus, processor 38 is able to calculate the fluid flow rate according to expression (2).

Processor 38 may use the derived value of the fluid flow rate as is described above for flowchart 200.

As shown by a line 420 in the flowchart, steps 404-416 are reiterated, so that the fluid flow rate is continuously monitored during the procedure performed by physician 15. The reiteration may be implemented by moving the period of time $T_p$, i.e., the window of this time. In a disclosed example the reiteration rate, corresponding to the time shift of the window, is in a range of approximately 3 ms to approximately 1 s.

EXAMPLES

Example 1. An apparatus for determining a fluid flow rate in a channel (34a) of a phacoemulsification probe (12), comprising: a first pressure sensor (56), coupled with the channel at a first position; a second pressure sensor (58), coupled with the channel at a second position, at a preset distance measured along the channel from the first position, and wherein the fluid flows from the first position to the second position; and a processor (38), configured to: acquire from the first pressure sensor a first pressure profile of fluid passing the first pressure sensor, subsequent to acquiring the first pressure profile, acquire from the second pressure sensor a second pressure profile of fluid passing the second pressure sensor, cross-correlate the first pressure profile with the second pressure profile; identify a time delay between the first profile and second profile based on the cross-correlation; and calculate the fluid flow rate based on the time delay and the preset distance.

Example 2. The apparatus according to example 1, wherein the channel comprises an irrigation channel in the phacoemulsification probe.

Example 3. The apparatus according to example 2, wherein the phacoemulsification probe comprises a needle-sleeve combination, wherein at least a portion of the needle-sleeve combination is configured to be placed within an eye, and wherein the second position is proximate to the needle-sleeve combination.

Example 4. The apparatus according to example 1, wherein the channel comprises an aspiration channel in the phacoemulsification probe.

Example 5. The apparatus according to example 4, wherein the phacoemulsification probe comprises a needle-sleeve combination, wherein at least a portion of the needle-sleeve combination is configured to be placed within an eye, and wherein the first position is proximate to the needle-sleeve combination.

Example 6. The apparatus according to example 1, wherein the first indications comprise first pressures and respective time values for the first pressures, and the second indications comprise second pressures and respective time values for the second pressures.

Example 7. The apparatus according to example 1, wherein the processor is configured to correlate the first indications with the second indications by calculating a correlation coefficient relating the first indications with the second indications.

Example 8. The apparatus according to example 7, wherein the processor is configured to determine the time when the correlation coefficient is greater than or equal to 0.85.

Example 9. An apparatus for determining a fluid flow rate in a channel (34a) of a phacoemulsification probe (12), comprising: a first pressure sensor (56), coupled with the channel at a first position so as to couple the first pressure sensor with a fluid in the channel; a second pressure sensor (58), coupled with the channel at a second position, at a preset distance measured along the channel from the first position, so as to couple the second pressure sensor with the fluid in the channel, and wherein the fluid flows from the first position to the second position; and a processor (38), configured to: acquire from the first pressure sensor first indications of a first pressure profile of a portion of the fluid passing the first pressure sensor, simultaneously with acquiring the first indications, acquire from the second pressure sensor second indications of a second pressure profile of the fluid passing the second pressure sensor, analyze the first indications to identify a frequency thereof having a maximum power, and identify a first phase of the frequency, analyze the second indications to identify the frequency and a second phase of the frequency, and calculate the fluid flow rate based on the preset distance and a phase shift between the first phase and the second phase.

Example 10. The apparatus according to example 9, wherein analyzing the first indications comprises performing a first fast Fourier transform (FFT) on the first pressure changes, and wherein analyzing the second indications comprises performing a second FFT on the second pressure changes.

Example 11. The apparatus according to example 9, wherein the channel comprises an irrigation channel in the phacoemulsification probe.

Example 12. The apparatus according to example 11, wherein the phacoemulsification probe comprises a needle-sleeve combination, wherein at least a portion of the needle-sleeve combination is configured to be placed within an eye, and wherein the second position is proximate to the needle-sleeve combination.

Example 13. The apparatus according to example 9, wherein the channel comprises an aspiration channel in the phacoemulsification probe.

Example 14. The apparatus according to example 13, wherein the phacoemulsification probe comprises a needle-sleeve combination, wherein at least a portion of the needle-sleeve combination is configured to be placed within an eye, and wherein the first position is proximate to the needle-sleeve combination.

Example 15. The apparatus according to example 9, wherein the first indications comprise first pressures and respective time values for the first pressures, and the second indications comprise second pressures and respective time values for the second pressures.

Example 16. A method for determining a fluid flow rate in a channel (34a) of a phacoemulsification probe (12), comprising: coupling a first pressure sensor (56), at a first position of the channel so as to couple with fluid in the channel; coupling a second pressure sensor (58), at a second position of the channel, at a preset distance measured along the channel from the first position, so as to couple with the fluid in the channel, and wherein the fluid flows from the first position to the second position; acquiring from the first pressure sensor first indications of a first pressure profile of a portion of the fluid passing the first sensor; subsequent to acquiring the first indications, acquiring from the second pressure sensor second indications of a second pressure profile of the fluid passing the second sensor; correlating the first indications with the second indications so as to identify a time when the second indications of the second pressure changes correspond to the first indications of the first pressure changes of the portion of the fluid; and calculating the fluid flow rate based on the time and the preset distance.

Example 17. The method according to example 16, wherein the channel comprises an irrigation channel in the phacoemulsification probe.

Example 18. The method according to example 17, wherein the phacoemulsification probe comprises a needle-sleeve combination, wherein at least a portion of the needle-sleeve combination is configured to be placed within an eye, and wherein the second position is proximate to the needle-sleeve combination.

Example 19. The method according to example 16, wherein the channel comprises an aspiration channel in the phacoemulsification probe.

Example 20. The method according to example 19, wherein the phacoemulsification probe comprises a needle-sleeve combination, wherein at least a portion of the needle-sleeve combination is configured to be placed within an eye, and wherein the first position is proximate to the needle-sleeve combination.

Example 21. The method according to example 16, wherein the first indications comprise first pressures and respective time values for the first pressures, and the second indications comprise second pressures and respective time values for the second pressures.

Example 22. The method according to example 16, further comprising correlating the first indications with the second indications by calculating a correlation coefficient relating the first indications with the second indications.

Example 23. The method according to example 22, further comprising determining the time when the correlation coefficient is greater than or equal to 0.85.

Example 24. A method for determining a fluid flow rate in a channel (34a) of a phacoemulsification probe (12), comprising: coupling a first pressure sensor (56), at a first position of the channel so as to couple with fluid in the channel; coupling a second pressure sensor (58), at a second position of the channel, at a preset distance measured along the channel from the first position, so as to couple with the fluid in the channel, and wherein the fluid flows from the first position to the second position; acquiring from the first pressure sensor first indications of a first pressure profile of a portion of the fluid passing the first pressure sensor; simultaneously with acquiring the first indications, acquiring from the second pressure sensor second indications of a second pressure profile of the fluid passing the second pressure sensor; analyzing the first indications to identify a frequency thereof having a maximum power, and identifying a first phase of the frequency; analyzing the second indications to identify the frequency and a second phase of the frequency; and calculating the fluid flow rate based on the preset distance and a phase shift between the first phase and the second phase.

Example 25. The method according to example 24, wherein analyzing the first indications comprises performing a first fast Fourier transform (FFT) on the first pressure changes, and wherein analyzing the second indications comprises performing a second FFT on the second pressure changes.

Example 26. The method according to example 24, wherein the channel comprises an irrigation channel in the phacoemulsification probe.

Example 27. The method according to example 26, wherein the phacoemulsification probe comprises a needle-sleeve combination, wherein at least a portion of the needle-sleeve combination is configured to be placed within an eye, and wherein the second position is proximate to the needle-sleeve combination.

Example 28. The method according to example 24, wherein the channel comprises an aspiration channel in the phacoemulsification probe.

Example 29. The method according to example 28, wherein the phacoemulsification probe comprises a needle-sleeve combination, wherein at least a portion of the needle-sleeve combination is configured to be placed within an eye, and wherein the first position is proximate to the needle-sleeve combination.

Example 30. The method according to example 24, wherein the first indications comprise first pressures and respective time values for the first pressures, and the second indications comprise second pressures and respective time values for the second pressures.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

The invention claimed is:

1. An apparatus for determining a fluid flow rate in a channel of a phacoemulsification probe, comprising:

a first pressure sensor, coupled with the channel at a first position;

a second pressure sensor, coupled with the channel at a second position, at a preset distance measured along the channel from the first position, and wherein the fluid flows from the first position to the second position; and a processor, configured to:

acquire from the first pressure sensor a first pressure profile of fluid passing the first pressure sensor, subsequent to acquiring the first pressure profile, acquire from the second pressure sensor a second pressure profile of fluid passing the second pressure sensor, cross-correlate the first pressure profile with the second pressure profile;

identify a time delay between the first profile and second profile based on the cross-correlation; and calculate the fluid flow rate based on the time delay and the preset distance.

2. The apparatus according to claim 1, wherein the channel comprises an irrigation channel in the phacoemulsification probe.

3. The apparatus according to claim 2, wherein the phacoemulsification probe comprises a needle-sleeve combination, wherein at least a portion of the needle-sleeve combination is configured to be placed within an eye, and wherein the second position is proximate to the needle-sleeve combination.

4. The apparatus according to claim 1, wherein the channel comprises an aspiration channel in the phacoemulsification probe.

5. The apparatus according to claim 4, wherein the phacoemulsification probe comprises a needle-sleeve combination, wherein at least a portion of the needle-sleeve combination is configured to be placed within an eye, and wherein the first position is proximate to the needle-sleeve combination.

6. The apparatus according to claim 1, wherein the first pressure profile comprises first pressures and respective time values for the first pressures, and the second pressure profile comprises second pressures and respective time values for the second pressures.

7. The apparatus according to claim 1, wherein the processor is configured to correlate the first pressure profile with the second pressure profile by calculating a correlation coefficient relating the first pressure profile with the second pressure profile.

8. The apparatus according to claim 7, wherein the processor is configured to determine the time when the correlation coefficient is greater than or equal to 0.85.

9. An apparatus for determining a fluid flow rate in a channel of a phacoemulsification probe, comprising:

a first pressure sensor, coupled with the channel at a first position so as to couple the first pressure sensor with a fluid in the channel;

a second pressure sensor, coupled with the channel at a second position, at a preset distance measured along the channel from the first position, so as to couple the second pressure sensor with the fluid in the channel, and wherein the fluid flows from the first position to the second position; and a processor, configured to:

acquire from the first pressure sensor first indications of a first pressure profile of a portion of the fluid passing the first pressure sensor, simultaneously with acquiring the first indications, acquire from the second pressure sensor second indications of a second pressure profile of the fluid passing the second pressure sensor, analyze the first indications to identify a frequency thereof having a maximum power, and identify a first phase of the frequency, analyze the second indications to identify the frequency and a second phase of the frequency, and calculate the fluid flow rate based on the preset distance and a phase shift between the first phase and the second phase.

10. The apparatus according to claim 9, wherein analyzing the first indications comprises performing a first fast Fourier transform (FFT) on the first pressure changes, and wherein analyzing the second indications comprises performing a second FFT on the second pressure changes.

11. The apparatus according to claim 9, wherein the channel comprises an irrigation channel in the phacoemulsification probe.

12. The apparatus according to claim 11, wherein the phacoemulsification probe comprises a needle-sleeve combination, wherein at least a portion of the needle-sleeve combination is configured to be placed within an eye, and wherein the second position is proximate to the needle-sleeve combination.

13. The apparatus according to claim 9, wherein the channel comprises an aspiration channel in the phacoemulsification probe.

14. The apparatus according to claim 13, wherein the phacoemulsification probe comprises a needle-sleeve combination, wherein at least a portion of the needle-sleeve combination is configured to be placed within an eye, and wherein the first position is proximate to the needle-sleeve combination.

15. The apparatus according to claim 9, wherein the first indications comprise first pressures and respective time values for the first pressures, and the second indications comprise second pressures and respective time values for the second pressures.

16. A method for determining a fluid flow rate in a channel of a phacoemulsification probe, comprising:

coupling a first pressure sensor, at a first position of the channel so as to couple with fluid in the channel;

coupling a second pressure sensor, at a second position of the channel, at a preset distance measured along the channel from the first position, so as to couple with the fluid in the channel, and wherein the fluid flows from the first position to the second position;

acquiring from the first pressure sensor first indications of a first pressure profile of a portion of the fluid passing the first sensor;

subsequent to acquiring the first indications, acquiring from the second pressure sensor second indications of a second pressure profile of the fluid passing the second sensor;

correlating the first indications with the second indications so as to identify a time when the second indications of the second pressure changes correspond to the first indications of the first pressure changes of the portion of the fluid; and calculating the fluid flow rate based on the time and the preset distance.

17. The method according to claim 16, wherein the channel comprises an irrigation channel in the phacoemulsification probe.

18. The method according to claim 17, wherein the phacoemulsification probe comprises a needle-sleeve combination, wherein at least a portion of the needle-sleeve combination is configured to be placed within an eye, and wherein the second position is proximate to the needle-sleeve combination.

19. The method according to claim 16, wherein the channel comprises an aspiration channel in the phacoemulsification probe.

20. The method according to claim 19, wherein the phacoemulsification probe comprises a needle-sleeve combination, wherein at least a portion of the needle-sleeve combination is configured to be placed within an eye, and wherein the first position is proximate to the needle-sleeve combination.

21. The method according to claim 16, wherein the first indications comprise first pressures and respective time values for the first pressures, and the second indications comprise second pressures and respective time values for the second pressures.

22. The method according to claim 16, further comprising correlating the first indications with the second indications by calculating a correlation coefficient relating the first indications with the second indications.

23. The method according to claim 22, further comprising determining the time when the correlation coefficient is greater than or equal to 0.85.

24. A method for determining a fluid flow rate in a channel of a phacoemulsification probe, comprising:

coupling a first pressure sensor, at a first position of the channel so as to couple with fluid in the channel;

coupling a second pressure sensor, at a second position of the channel, at a preset distance measured along the channel from the first position, so as to couple with the fluid in the channel, and wherein the fluid flows from the first position to the second position;

acquiring from the first pressure sensor first indications of a first pressure profile of a portion of the fluid passing the first pressure sensor;

simultaneously with acquiring the first indications, acquiring from the second pressure sensor second indications of a second pressure profile of the fluid passing the second pressure sensor;

analyzing the first indications to identify a frequency thereof having a maximum power, and identifying a first phase of the frequency;

analyzing the second indications to identify the frequency and a second phase of the frequency; and calculating the fluid flow rate based on the preset distance and a phase shift between the first phase and the second phase.

25. The method according to claim 24, wherein analyzing the first indications comprises performing a first fast Fourier transform (FFT) on the first pressure changes, and wherein analyzing the second indications comprises performing a second FFT on the second pressure changes.

26. The method according to claim 24, wherein the channel comprises an irrigation channel in the phacoemulsification probe.

27. The method according to claim 26, wherein the phacoemulsification probe comprises a needle-sleeve combination, wherein at least a portion of the needle-sleeve combination is configured to be placed within an eye, and wherein the second position is proximate to the needle-sleeve combination.

28. The method according to claim 24, wherein the channel comprises an aspiration channel in the phacoemulsification probe.

29. The method according to claim 28, wherein the phacoemulsification probe comprises a needle-sleeve combination, wherein at least a portion of the needle-sleeve combination is configured to be placed within an eye, and wherein the first position is proximate to the needle-sleeve combination.

30. The method according to claim 24, wherein the first indications comprise first pressures and respective time values for the first pressures, and the second indications comprise second pressures and respective time values for the second pressures.

* * * * *